(12) United States Patent
Clark et al.

(10) Patent No.: US 7,098,238 B2
(45) Date of Patent: Aug. 29, 2006

(54) DEGRADATION FRAGMENTS

(75) Inventors: Joseph Floyd Clark, Cincinnati, OH (US); Thomas Andrew Daniel Cadoux-Hudson, Oxford (GB); Christopher Joseph Schofield, Oxford (GB)

(73) Assignee: Medical Research Council, London (GB)

( * ) Notice: Subject to any disclaimer, the term of this patent is extended or adjusted under 35 U.S.C. 154(b) by 61 days.

(21) Appl. No.: 10/204,950

(22) PCT Filed: Feb. 26, 2001

(86) PCT No.: PCT/GB01/00830

§ 371 (c)(1),
(2), (4) Date: Mar. 7, 2003

(87) PCT Pub. No.: WO01/62245

PCT Pub. Date: Aug. 30, 2001

(65) Prior Publication Data

US 2003/0162826 A1 Aug. 28, 2003

(30) Foreign Application Priority Data

Feb. 25, 2000 (GB) ................................ 0004549.2

(51) Int. Cl.
*A61K 31/4025* (2006.01)
*C07D 207/18* (2006.01)
(52) U.S. Cl. ...................... 514/422; 548/518; 548/530; 548/537; 548/541; 548/543; 514/423; 514/424; 530/387.1
(58) Field of Classification Search ................ 548/518, 548/530, 537, 541, 543; 514/422, 423, 424; 530/387.1
See application file for complete search history.

(56) References Cited

U.S. PATENT DOCUMENTS

| | | |
|---|---|---|
| 3,989,625 A | 11/1976 | Mason |
| 4,301,075 A | 11/1981 | Lohmann et al. |
| 5,380,667 A | 1/1995 | Schwertner |

FOREIGN PATENT DOCUMENTS

| | | |
|---|---|---|
| EA | 0 747 002 A1 | 12/1996 |
| EP | 0 829 262 A2 | 3/1998 |
| JP | 06-256308 | 9/1994 |
| JP | 08-151365 | 6/1996 |
| JP | 09-268174 | 10/1997 |
| WO | WO 93/22309 | 11/1993 |
| WO | IB-96/29974 A2 | 10/1996 |
| WO | IB-97/39353 A1 | 10/1997 |

OTHER PUBLICATIONS

XP-002169623: Abstract—Pure maleimide or derivative preparation—by de:carbamoylation of N-carbamoyl analogue with tertiary amine, used e.g. as drug intermediate or polymer starting material; AN—1997-554696(51).
AN—1995:742172 CAPLUS; Abstract—Conformational enantiomerism of bilirubin and pamoic acid induced by protonated amino cyclodextrine; ER 2 of 2.
AN—1996:344355 CAPLUS; Abstract—Stereocontrol of bilirubin conformation; ER 1 of 2.

(Continued)

*Primary Examiner*—Golam M. M. Shameem
(74) *Attorney, Agent, or Firm*—Fulbright & Jaworski L.L.P.

(57) ABSTRACT

A pharmaceutical composition comprising a compound of formula (I) wherein X is an electron withdrawing group, $Y^1$ is hydrogen, alkyl, alkenyl, alkynyl, aryl, heterocyclyl, $-SO_2R^4$, $-CO_2R^4$, $-CONHR^4$ or $-COR^4$, and each of $R^1$, $R^2$ and $R^4$, which may be the same or different, is hydrogen, alkyl, cycloalkyl, alkenyl, cycloalkenyl, alkynyl, aryl or heterocyclyl, or a compound of formula (II) wherein each of $Y^2$ and $Y^3$, which may be the same or different, is hydrogen, alkyl, alkenyl, alkynyl, aryl, heterocyclyl, $-SO_2R^9$, $-CO_2R^9$, $-CONHR^9$ or $-COR^9$, Z is hydrogen, alkyl, cycloalkyl, alkenyl, cycloalkenyl, alkynyl, aryl, heterocyclyl, $-CH=C(NHR_{10})CH((CH_2)_mCO_2R^{11})(C=O)CH_3$ or $-CH_2(C=O)CH((CH_2)_mCO_2R^{11})(C=O)CH_3$, $R^8$ is $-(CH_2)_nCO_2R^{12}$, each of $R^5$ to $R^7$ and $R^9$ to $R^{12}$, which may be the same or different, is hydrogen, alkyl, cycloalkyl, alkenyl, cycloalkenyl, alkynyl, aryl or heterocyclyl, and each of m and n, which may be the same or different, is 1 to 6 or a compound of formula (III) wherein each of $Y^4$ to $Y^6$, which may be the same or different, is hydrogen, alkyl, alkenyl, alkynyl, aryl, heterocyclyl, $-SO_2R^{19}$, $-CO_2R^{19}$, $-CONHR^{19}$ or $-COR^{19}$, each of $R^{16}$ and $R^{17}$, which may be the same or different, is $-(CH_2)_pCO_2R^{20}$, each of $R^{13}$ TO $R^{15}$ and $R^{18}$ to $R^{20}$, which may be the same or different, is hydrogen, alkyl, cycloalkyl, alkenyl, cycloalkenyl, alkynyl, aryl or heterocyclyl, and p is 1 to 6, or other photolabile degradation product of bilirubin or biliverdin or derivative of a photolabile degradation fragment of bilirubin or biliverdin, or a pharmaceutically acceptable salt thereof, together with a pharmaceutically acceptable carrier or diluent

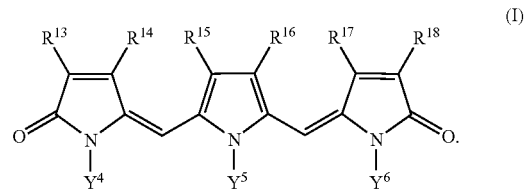

4 Claims, 6 Drawing Sheets

OTHER PUBLICATIONS

AN—1972:137252 CAPLUS; Abstract—Methylvinylmaleimide from bilirubin photoxidation; SWER 8 of 8.

Clark, Joseph F., et al.; Phosphocreatine and Creatine Kinase in Energetic Metabolism of the Porcine Cartoid Artery; J Vasc Res 1995; 32:24-30.

Continuous cultures of fused cells secreting antibody of predefined specificity; Nature, vol. 256, pp. 495-497, Aug. 7, 1975.

Fulton, David et al. Role of Phospholipase C and Phospholipase A2 in the Nitric Oxide-Independent Vasodilator Effect of Bradykinin in the Rat Perfused Heart; *The Journal of Pharmacology and Experimental Therapeutics*; vol. 278, No. 2; pp. 518-526, 1996.

Lasley, Robert et al. Effects of Protein Kinase C INhibitors in In Situ and Isolated Ischemic Rabbit Myocardium; *J. Mol Cell Cardiol 29*, 3345-3356; 1997.

Lightner, David et al. Bilirubin Photooxidation Products in the Urine of Jaundiced Neonates Receiving Phototherapy; *Pediatric Research*, vol. 18, No. 8, pp. 698-700; 1984.

Abstract—Database WPI; Derwent Publications Ltd. London, GB AN 1994-330011; XP002169623; Oct. 1997.

Abstract—Database WPI; Derwent Publications Ltd. London, GB; An 1996-329455; XP002169621; Jun. 1996.

Yamaguchi, Tokio et al.; Chemical STructure of a New FAmily of Bile Pigments from Human Urine; *J. Biochem*, 116, 298-303; 1994.

Gray, C.H. et al. The Photodecompositinon of Bilirubin and Other Bile Pigments; *J. Chem. Soc. Perkin Trans.* vol. 1, pp. 288-294, 1972.

Kranc, Kamil R. et al.; Oxidative degradation of bilirubin produces vasoactive combounds; *Eur. J. Biochem*, 267, pp. 7094-7101, 2000.

Clark et al., "Oxidation of Bilirubin Produces Compounds That Cause Prolonged Vasospasm of Rat Cerebral Vessels: A Contributor to Subarachnoid Hermorrhage-Induced Vasospasm," *J. Cerebral Blood Flow & Metabolism*, 22: 472-478, 2002.

Lowe, "Chemoselective biosensors," *Curr. Opin. Chem. Biol.*, 3: 108-111, 1999.

Nerbonne, "Design and Application of Photolabile Intracellular Probes," *Soc. Gen. Physiol. Ser.*, 40: 417-45, 1986.

Osborne et al., "Aptamers as therapeutic and diagnostic reagents: problems: problems and prospects," *Curr. Opin. Chem. Biol.*, 1: 5-9, 1997.

Rogers, "Principles of Affinity-Based Biosensors," *Mol. Biotechnol.*, 14: 109-129, 2000.

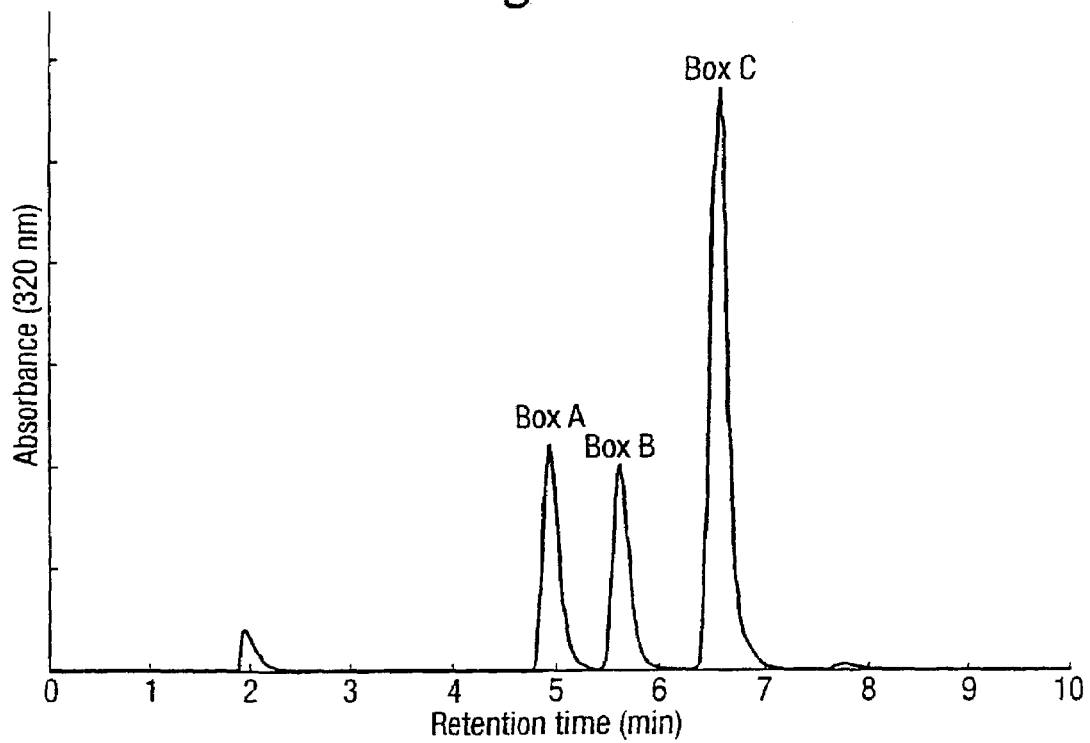

DEGRADATION FRAGMENTS

This Application is the National Phase Application of International Application No. PCT/GB01/00830 filed Feb. 26, 2001 which claims priority to Great Britain Application No. 0004549.2 filed Feb. 25, 2000.

The present invention relates to degradation fragments of bilirubin or biliverdin, to their derivatives and to their use.

Erythrocyte lysis (haemolysis) may follow subarachnoid haemorrhage (SAH), a type of haemorrhagic stroke in which delayed ischemic complications is a major factor affecting patient outcome. Haemolysate components such as oxyhaemoglobin, methemoglobin, hemin and bilirubin (BR) are found in cerebral spinal fluid (CSF) from patients with SAH. SAH induced by subarachnoid injections of lysed blood up regulates expression of haem oxygenase-1 (HO-1), an inducible isoform of haem oxygenase, in glia throughout the brain HO-1 catalyses the degradation of haem resulting in release of biliverdin, CO and free iron and HO-1 expression is a limiting step in the haemoglobin degradation pathway. Biliverdin is subsequently reduced by biliverdin reductase to form BR, a reductant which scavenges reactive oxygen species. Due to its antioxidant activity, BR can serve as a protective agent in cells, membrane lipids and low density lipoproteins (LDL) exposed to oxidative stress. High levels of BR can be found in subarachnoid clots in the perivascular area and in CSF during SAH ($CSF_{SAH}$) and SAH induced cerebral vasospasm.

Biochemical and clinical studies have indicated a role for oxygen free radicals in the pathogenesis of vasospasm and neurological dysfunction following SAH. Oxyhaemoglobin, a major constituent of haemolysate, is a potent generator of reactive oxygen species. Increases in both enzymatic (arachidonic acid cascade and eicosanoid peroxide production) and non-enzymatic (thiobarbituric acid reactive substances production and cholesteryl ester hydroperoxides) lipid peroxidation products have been found in models of SAH, suggesting a role for oxidative stress during SAH.

Cells exposed to oxidative stress have increased activity of inducible isoform of HO-1 resulting in elevated BR levels. HO-1 upregulation is associated with vasious pathological states including cerebral haemorrhage, cerebral vasospasm following SAH, ischemic-reperfusion and endotoxemia. Although the presence of BR in CSF from patients with SAH has been confirmed, BR per se failed to develop significant arterial spasm in vivo. Therefore, its role in SAH, pathogenesis of vasospasm and complications due to vasospasm has remained uncertain.

Generation of reactive oxygen species within the subarachnoid space following SAH leads to HO-1 upregulation and release of biliverdin and BR, which may serve as targets for reactive oxygen species-mediated degradation. Under pathological conditions of severe oxidative stress, the oxidative degradation of BR and biliverdin may occur to give compounds causing vasospasm following SAH.

The term "vasospasm" as used herein means contraction of blood vessels particularly in association with the brain.

The term "vasoconstriction" as used herein means contraction of the blood vessels particularly in association with organs other than the brain.

The present invention concerns degradation fragments of bilirubin or biliverdin which may be produced under pathological conditions of severe oxidative stress, and their derivatives.

In one aspect the present invention provides a pharmaceutical composition comprising a compound of formula (I)

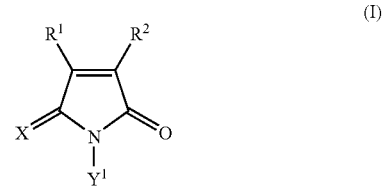

wherein X is an electron withdrawing group typically connected to the ring via an oxygen or carbon atom, such as =O, =CH(C=O)$R^3$, =CH(C=O)$OR^3$ or =CH(C=O)NH$R^3$, $Y^1$ is hydrogen, alkyl, alkenyl, alkynyl, aryl, heterocyclyl, —$SO_2R^4$, —$CO_2R^4$, —CONH$R^4$ or —$COR^4$, and each of $R^1$ to $R^4$, which may be the same or different, is hydrogen, alkyl, cycloalkyl, alkenyl, cycloalkenyl, alkynyl, aryl or heterocyclyl, or A Compound of Formula (II)

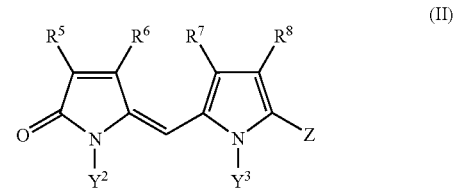

wherein each of $Y^2$ and $Y^3$, which may be the same or different, is hydrogen, alkyl, alkenyl, alkynyl, aryl, heterocyclyl, —$SO_2R^9$, —$CO_2R^9$, —CONH$R^9$ or —$COR^9$, Z is hydrogen, alkyl, cycloalkyl, alkenyl, cycloalkenyl, alkynyl, aryl, heterocyclyl, —CH=C(NH$R^{10}$)CH(($CH_2$)$_m$$CO_2R^{11}$)(C=O)$CH_3$ or —$CH_2$(C=O)CH(($CH_2$)$_m$$CO_2R^{11}$)(C=O)$CH_3$, $R^8$ is —($CH_2$)$_n$$CO_2R^{12}$, each of $R^5$ to $R^7$ and $R^9$ to $R^{12}$ which may be the same or different, is hydrogen, alkyl, cycloalkyl, alkenyl, cycloalkenyl, alkynyl, aryl or heterocyclyl, and each of m and n, which may be the same or different, is 1 to 6, or A Compound of Formula (III)

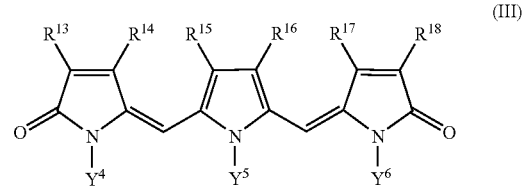

wherein each of $Y^4$ to $Y^6$, which may be the same or different, is hydrogen, alkyl, alkenyl, alkynyl, aryl, heterocyclyl, —$SO_2R^{19}$, —$CO_2R^{19}$, —CONH$R^{19}$ or —$COR^{19}$, each of $R^{16}$ and $R^{17}$, which may be the same or different, is —($CH_2$)$_p$$CO_2R^{20}$, each of $R^{13}$ to $R^{15}$ and $R^{18}$ to $R^{20}$, which may be the same or different, is hydrogen, alkyl, cycloalkyl, alkenyl, cycloalkenyl, alkynyl, aryl or heterocyclyl, and p is 1 to 6, or other photolabile degradation product of bilirubin or biliverdin or derivative of a photolabile degradation product of bilirubin or biliverdin, or a pharmaceutically acceptable salt thereof, together with a pharmaceutically acceptable carrier or diluent.

It will be appreciated that $R^1$ to $R^{20}$, $X$, $Y^1$ to $Y^6$ and $Z$ can be combinations of the specified groups.

The term "alkyl" as used herein includes both unsubstituted and substituted, straight and branched chain radicals. Typically it is $C_1$–$C_6$ alkyl, preferably $C_1$–$C_4$ alkyl, for example methyl, ethyl, i-propyl, n-propyl, t-butyl, s-butyl or n-butyl. It may also be pentyl, hexyl and the various branched chain isomers thereof. When the alkyl group is substituted it typically bears one or more substituents selected from aryl, cycloalkyl, halogen, trihaloalkyl such as trifluoromethyl, hydroxyl, alkoxyl, aralkoxyl, amino, mono or dialkylamino, nitro, cyano, carbonyl, carboxyl, alkylsulphoxyl or alkylsulphonyl.

The term "cycloalkyl" as used herein typically means a cycloalkyl group having 3 to 8 carbons, for example cyclopropyl, cyclopentyl, cyclohexyl and cyclooctyl. A cycloalkyl group may be unsubstituted or substituted as the alkyl groups above.

The term "alkenyl" as used herein includes unsubstituted and substituted, straight and branched chain radicals having one or more double bonds. Typically it is $C_2$–$C_6$ alkenyl such as, for example, allyl, butenyl, butadienyl, pentenyl or hexenyl. When the alkenyl group is substituted it typically bears one or more substituents as defined above for the alkyl groups.

The term "cycloalkenyl" as used herein typically means a cycloalkenyl group having 4 to 8 carbons, for example cyclopentenyl, cyclohexenyl or cyclooctadienyl.

The term "alkynyl" as used herein includes unsubstituted and substituted, straight and branched chain radicals having one or more triple bonds. Typically it is $C_2$–$C_6$ alkynyl, such as butynyl. When the alkynyl group is substituted it typically bears one or more substituents as defined above for the alkyl groups.

The term "aryl" as used herein includes both monocyclic and bicyclic aromatic groups which typically contain from 6 to 10 carbons in the ring portion, such as phenyl or naphthyl. The aryl group is unsubstituted or substituted. When it is substituted the aryl group may be substituted by, for example, one or more substituents selected from $C_1$–$C_6$ alkyl, $C_1$–$C_6$ alkoxyl, trihaloalkyl such as trifluoromethyl, halogen and hydroxyl.

The term "heterocyclyl" as used herein is typically a 3- to 10-membered, saturated or unsaturated heterocyclic ring containing at least one heteroatom selected from N, O and S and which is optionally fused to a second 5- or 6-membered, saturated or unsaturated heterocyclic ring or to an aryl group as defined above. The heterocyclic ring may be, for example, pyridine, furan, thiophene, pyrrole, pyrrolidine, pyrimidine, pyrazine, pyridazine, pyrazole or indazole, or a cyclic ether such as glucose. The heterocyclyl group may be unsubstituted or substituted at any position. Suitable substituents include alkyl, for example haloalkyl, aryl, for example phenyl, halogen and hydroxyl.

The term "halogen" as used herein means fluorine, chlorine, bromine and iodine.

The term "aralkyl" as used herein refers to alkyl groups as previously defined having an aryl substituent, for example benzyl, phenylethyl, diphenylmethyl and triphenylmethyl.

The term "alkoxyl" or "aralkoxyl" as used herein includes any of the above alkyl, cycloalkyl or aralkyl groups linked to an oxygen atom.

Preferably, $X$ is $=O$ or $=CH(C=O)NHR^3$ wherein $R^3$ is hydrogen or alkyl. More preferably, $X$ is $=O$ or $=CH(C=O)NH_2$.

Preferably, $Y^1$ is hydrogen.

Each of $R^1$ and $R^2$ is preferably hydrogen, alkyl or alkenyl. More preferably, one of $R^1$ and $R^2$ is hydrogen or alkyl and the other is alkenyl. Still more preferably, one of $R^1$ and $R^2$ is methyl and the other is $—CH=CH_2$.

Preferably, each of $Y^2$ and $Y^3$ is hydrogen.

$Z$ is preferably $—CH=C(NHR^{10})CH((CH_2)_mCO_2R^{11})(C=O)CH_3$ or $—CH_2(C=O)CH((CH_2)_mCO_2R^{11})(C=O)CH_3$ wherein each of $R^{10}$ and $R^{11}$ is hydrogen or alkyl and m is 1 to 6. More preferably, $Z$ is $—CH=C(NHR^{10})CH((CH_2)_mCO_2R^{11})(C=O)CH_3$ or $—CH_2(C=O)CH((CH_2)_mCO_2R^{11})(C=O)CH_3$ wherein each of $R^{10}$ and $R^{11}$ is hydrogen or alkyl and m is 1 to 4. Still more preferably, $Z$ is $—CH=C(NH_2)CH((CH_2)_2CO_2H)(C=O)CH_3$ or $—CH_2(C=O)CH((CH_2)_2CO_2H)(C=O)CH_3$.

Each of $R^5$ to $R^7$ is preferably hydrogen, alkyl or alkenyl. More preferably, one of $R^5$ and $R^6$ is hydrogen or alkyl and the other is alkenyl, and $R^7$ is alkyl. Still more preferably, one of $R^5$ and $R^6$ is methyl and the other is $—CH=CH_2$, and $R^7$ is methyl.

Preferably, $R^8$ is $—(CH_2)_2CO_2R^{12}$ wherein $R^{12}$ is hydrogen or alkyl. More preferably, $R^8$ is $—(CH_2)CO_2H$.

Preferably, each of $Y^4$ to $Y^6$ is hydrogen.

Each of $R^{13}$ to $R^{15}$ and $R^{18}$ is preferably hydrogen, alkyl or alkenyl. More preferably, one of $R^{13}$ and $R^{14}$ is hydrogen or alkyl and the other is alkenyl, and each of $R^{15}$ and $R^{18}$ is alkyl. Still more preferably, one of $R^{13}$ and $R^{14}$ is methyl and the other is $—CH=CH_2$, and each of $R^{15}$ and $R^{18}$ is methyl.

Preferably, each of $R^{16}$ and $R^{17}$ is $—(CH_2)_2CO_2R^{20}$ wherein $R^{20}$ is hydrogen or alkyl. More preferably, each of $R^{16}$ and $R^{17}$ is $—(CH_2)_2CO_2H$.

Preferred compositions of the invention are compositions wherein in formula (I) $X$ is $=O$ or $=CH(C=O)NHR^3$, $Y^1$ is as defined above, each of $R^1$ and $R^2$, which may be the same or different, is hydrogen, alkyl or alkenyl and $R^3$ is hydrogen or alkyl, or in formula (II) each of $Y^2$ and $Y^3$ is as defined above, $Z$ is $—CH=C(NHR^{10})CH((CH_2)_mCO_2R^{11})(C=O)CH_3$ or $—CH_2(C=O)CH((CH_2)_mCO_2R^{11})(C=O)CH_3$, each of $R^5$ to $R^7$ is hydrogen, alkyl or alkenyl, $R^8$ is $—(CH_2)_2CO_2R^{12}$, each of $R^{10}$ to $R^{12}$ is hydrogen or alkyl and m is 1 to 6, or in formula (III) each of $Y^4$ to $Y^6$ is as defined above, each of $R^{13}$ to $R^{15}$ and $R^{18}$ are hydrogen, alkyl or alkenyl, each of $R^{16}$ and $R^{17}$ is $—(CH_2)_2CO_2R^{20}$ and $R^{20}$ is hydrogen or alkyl.

More preferred compositions of the invention are compositions wherein in formula (I) when $X$ is $=CH(C=O)NH_2$, $Y^1$ is hydrogen, and one of $R^1$ and $R^2$ is hydrogen or alkyl and the other is alkenyl, or when $X$ is $=O$, $Y^1$ is hydrogen, $R^1$ is alkenyl and $R^2$ is hydrogen or alkyl, or in formula (II) each of $Y^2$ and $Y^3$ is hydrogen, $Z$ is $—CH=C(NHR^{10})CH((CH_2)_mCO_2R^{11})(C=O)CH_3$ or $—CH_2(C=O)CH((CH_2)_mCO_2R^{11})(C=O)CH_3$, one of $R^5$ and $R^6$ is hydrogen or alkyl and the other is alkenyl, $R^7$ is alkyl, $R^8$ is $(CH_2)_2CO_2H$, each of $R^{10}$ and $R^{11}$ is hydrogen or alkyl and m is 1 to 4, or in formula (III) each if $Y^4$ to $Y^6$ is hydrogen, one of $R^{13}$ and $R^{14}$ is hydrogen or alkyl and the other is alkenyl, each of $R^{15}$ and $R^{18}$ is hydrogen or alkyl and each of $R^{16}$ and $R^{17}$ is $—(CH_2)_2CO_2H$.

Still more preferred compositions of the invention are compositions wherein in formula (I) when $X$ is $=CH(C=O)NH_2$, $Y^1$ is hydrogen, and one of $R^1$ and $R^2$ is methyl and the other is $—CH=CH_2$, or when $X$ is $=O$, $Y^1$ is hydrogen, $R^1$ is $—CH=CH_2$ and $R^2$ is methyl, or in formula (II) each of $Y^2$ and $Y^3$ is hydrogen, Z is —CH═C($NH_2$)CH(($CH_2$)$_2$$CO_2$H)(C═O)$CH_3$ or —$CH_2$(C═O)CH(($CH_2$)$_2$$CO_2$H)(C═O)$CH_3$, one of $R^5$ and $R^6$ is methyl and the other is —CH═$CH_2$, $R^7$ is methyl and $R^8$ is —($CH_2$)$_2$$CO_2$H or in formula (III) each of $Y^4$ to $Y^6$ is hydrogen, one of $R^{13}$ and $R^{14}$ is methyl and the other is —CH═$CH_2$, each of $R^{15}$ and $R^{18}$ is methyl and each of $R^{16}$ and $R^{17}$ is —($CH_2$)$_2$$CO_2$H.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutical acceptable bases include alkali metal (e.g. sodium or potassium) and alkali earth metal (e.g. calcium or magnesium) hydroxides and organic bases such as alkyl amines, aralkyl amines or heterocyclyl amines.

The present invention includes all possible isomers of the compounds of formula (I), (II) or (III), or the other photolabile degradation fragments of bilirubin or biliverdin, and mixtures thereof, including cis and trans alkene isomers, and diastereomeric mixtures and racemic mixtures, resulting from the possible combinations of (R) and (S) stereochemistry when stereogenic centres are present.

In another aspect the present invention provides novel degradation fragments of bilirubin or biliverdin or derivatives of degradation fragments of bilirubin or biliverdin. Thus, the present invention provides a compound of formula (I), (II) or (III) as defined above, or other degradation fragment of bilirubin or biliverdin or derivative of a degradation fragment of bilirubin or biliverdin, or a salt thereof, excluding a compound of formula (I) wherein X is ═O, $Y^1$ is hydrogen, $R^1$ is —CH═$CH_2$ and $R^2$ is methyl, or a compound of formula (III) wherein each of $Y^4$ to $Y^6$ is hydrogen, one of $R^{13}$ or $R^{14}$ is methyl and the other is —CH═$CH_2$, each of $R^{15}$ and $R^{18}$ is methyl and each of $R^{16}$ and $R^{17}$ is —($CH_2$)$_2$$CO_2$H. Suitable salts include those mentioned above as examples of pharmaceutically acceptable salts.

The compounds of formula (I), (II) or (III), or the other degradation fragments of bilirubin or biliverdin or derivatives of degradation fragments of bilirubin or biliverdin, or salts thereof, according to the present invention may be prepared by synthetic methods known in the art. They may also be prepared by a process comprising reaction of bilirubin or biliverdin with an oxidising reagent, for example oxygen, hydrogen peroxide, potassium permanganate, osmium tetroxide, chromium (VI) oxide or sodium periodate. Catalysts such as transition metals may be employed in the process. Bilirubin or biliverdin may suitably be dissolved in an alkali such as sodium or potassium hydroxide, for example 1 to 5M sodium hydroxide. The solution may then be neutralized using, for example, hydrochloric acid such as 5 to. 11M HCl, acetic acid, perchloric acid, nitric acid or sulphuric acid. The resulting solution may then be contacted with a free radical or reactive species. The degradation fragments thus obtained may be extracted, purified and modified, as desired, by methods well known to those skilled in the art.

The pharmaceutical compositions of the present invention may be prepared in a conventional way by employing conventional non-toxic pharmaceutical carriers or diluents in a variety of dosage forms and ways of administration The compositions may, for example, be administered parenterally, either subcutaneously or intravenously or intramuscularly, or intrasternally, or by infusion techniques. The pharmaceutical compositions may be in the form of a sterile injectable aqueous or oleaginous suspensions.

These suspensions may be formulated according to the known art using suitable dispersing or wetting agents and suspending agents. The sterile injectable preparation may also be a sterile injectable solution or suspension in a non-toxic parenterally-acceptable diluent or solvent, for example a solution in 1,3-butanediol. Among the acceptable vehicles and solvents that may be employed are water, Ringer's solution and isotonic sodium chloride solution. In addition, sterile fixed oils are conventionally employed as a solvent or suspending medium.

For this purpose any bland fixed oils may be conventionally employed including synthetic mono or diglycerides. In addition fatty acids such as oleic acid find use in the preparation of injectables.

The dose varies according to the activity of the specific compound, the age, weight, and conditions of the subject to be treated, the type and the severity of the disease, and the frequency and route of administration. Typically the dose is from 0.0001 to 50 mg per kg of body weight. The amount of active ingredient that may be combined with the carrier materials to produce a single dosage form will vary depending upon the host treated and the particular mode of administration. Dosage unit forms will generally contain between from 5 to 500 mg of the active compound.

The compounds of formula (I), (II) and (III) and the other photolabile degradation fragments of bilirubin or biliverdin and derivatives of degradation fragments of bilirubin or biliverdin, and pharmaceutically acceptable salts thereof, have been found to induce vasospasm or vasoconstriction. The compositions according to the present invention may therefore find application in treating or inducing vasospasm or vasoconstriction. For example, the compositions of the present invention may be used in wound sealing such as peri-operative closure of vessels and incisions (either alone or in combination with conventional wound sealing methods), laceration or traumatic wound closing, or vessel closure following tissue or tumour resection. The compositions of the present invention may be in the form of opaque emulsions or suspensions so that during use degradation of the photolabile active compound by light is reduced. After surgery, or in the event that the composition is applied to the wrong site, the photolabile active compound may be degraded by irradiation of the treated site.

The, present invention thus provides a method of treating a patient in need of vasospasm or vasoconstriction, which method comprises administering to said patient a non-toxic and therapeutically effective amount of a compound of formula (I), (II) or (III), or other photolabile degradation fragment of bilirubin or biliverdin or derivative of a degradation fragment of bilirubin or biliverdin, or a pharmaceutically acceptable salt thereof. The condition of the patient may thereby be ameliorated.

In another aspect the present invention provides a compound of formula (I), (II) or (III), or other photolabile degradation fragment of bilirubin or biliverdin or derivative of a degradation fragment of bilirubin or biliverdin, or a pharmaceutically acceptable salt thereof, as defined above for use in a method of treatment of the human or animal body.

In another aspect the present invention provides use of a compound of formula (I), (II) or (III), or other photolabile degradation fragment of bilirubin or biliverdin or derivative of a degradation fragment of bilirubin or biliverdin, or a pharmaceutically acceptable salt thereof, as defined above in the manufacture of a medicament for use in treating or inducing vasospasm or vasoconstriction.

In another aspect the present invention provides a diagnostic composition comprising a compound of formula (I) as defined above wherein when X is $=CH(C=O)NH_2$, $Y^1$ is hydrogen, and one of $R^1$ and $R^2$ is methyl and the other is $-CH=CH_2$, or when X is $=O$, $Y^1$ is hydrogen, $R^1$ is $-CH=CH_2$ and $R^2$ is methyl, or a compound of formula (II) as defined above wherein each of $Y^2$ and $Y^3$ is hydrogen, Z is $-CH_2(C=O)CH((CH_2)_2CO_2H)(C=O)CH_3$, one of $R^5$ and $R^6$ is methyl and the other is $-CH=CH_2$, $R^7$ is methyl, $R^8$ is $(CH_2)_2CO_2H$, or a compound of formula (III) as defined above wherein one of $R^{13}$ and $R^{14}$ is methyl and the other is $-CH=CH_2$, each of $R^{15}$ and $R^{18}$ is methyl and each of $R^{16}$ and $R^{17}$ is $-(CH_2)_2CO_2H$, or other degradation fragment of bilirubin or biliverdin, or a salt thereof, and a diluent or carrier. Suitable salts include those mentioned above as examples of pharmaceutically acceptable salts.

In one embodiment the diagnostic composition comprises a photolabile degradation fragment of bilirubin or biliverdin.

In another aspect the present invention provides a method for diagnosing vasospasm or vasoconstriction in a host comprising determining the presence or absence of a compound of formula (I) as defined above wherein when X is $=CH(C=O)NH_2$, $Y^1$ is hydrogen, and one of $R^1$ and $R^2$ is methyl and the other is $-CH=CH_2$, or when X is $=O$, $Y^1$ is hydrogen, $R^1$ is $-CH=CH_2$ and $R^2$ is methyl, or a compound of formula (II) as defined above wherein each of $Y^2$ and $Y^3$ is hydrogen, Z is $-CH_2(C=O)CH((CH_2)_2CO_2H)(C=O)CH_3$, one of $R^5$ and $R^6$ is methyl and the other is $-CH=CH_2$, $R^7$ is methyl, $R^8$ is $(CH_2)_2CO_2H$, or a compound of formula (III) as defined above wherein one of $R^{13}$ and $R^{14}$ is methyl and the other is $-CH=CH_2$, each of $R^{15}$ and $R^{18}$ is methyl and each of $R^{16}$ and $R^{17}$ is $-(CH_2)_2CO_2H$, or other degradation fragment of bilirubin or biliverdin, or a salt thereof, wherein the presence of the compound of formula (I), (II) or (III), or the degradation fragment of bilirubin or biliverdin, or salt thereof, indicates that the host has vasospasm or vasoconstriction.

In one embodiment the method comprises
(a) contacting a sample from the host with an agent that binds to the compound of formula (I), (II) or (III), or the other degradation fragment of bilirubin or biliverdin, or salt thereof, and
(b) detecting whether the agent binds to components in the sample, thereby determining the presence or absence of the compound of formula (I), (II) or (III), or the other degradation fragment of bilirubin or biliverdin, or salt thereof.

The agent may be any agent capable of binding to the compound of formula (I), (II) or (III), or the other degradation fragment of bilirubin or biliverdin, or salt thereof, for example an antibody or a labelled antibody.

An antibody to the compound of formula (I), (II) or (III), or the other degradation fragment of bilirubin or biliverdin, or salt thereof, may be produced by raising antibody in a host animal against the whole or part of the compound of formula (I), (II) or (III), or the other degradation fragment of bilirubin or biliverdin, or salt thereof (hereinafter "the immunogen"). Methods of producing monoclonal and polyclonal antibodies are well-known. A method for producing a polyclonal antibody comprises immunising a suitable host animal, for example an experimental animal, with the immunogen and isolating immunoglobulins from the serum. The animal may therefore be inoculated with the immunogen, blood subsequently removed from the animal and the IgG fraction purified. A method for producing a monoclonal antibody comprises immortalising cells which produce the desired antibody. Hybridoma cells may be produced by fusing spleen cells from an inoculated experimental animal with tumour cells (Kohler and Milstein, Nature 256, 495–497, 1975).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat or mouse. If desired, the immunogen may be administered as a conjugate in which the immunogen is coupled to a suitable carrier. The carrier molecule is typically a physiologically acceptable carrier. The antibody obtained may be isolated and, if desired, purified.

The sample used in the method for diagnosing vasospasm or vasoconstriction according to the present invention may be any suitable sample from human or animal. The sample is typically a cerebral spinal fluid or blood sample. The sample may be processed before it is used in the method, for example it may be diluted, typically in water, saline or saline containing a buffer (any of these diluents may additionally comprise detergent).

An antibody used in the method of the invention may either be a whole antibody or a fragment thereof which is capable of binding the compound of formula (I), (II) or (III), or the other degradation fragment of bilirubin or biliverdin, or salt thereof. Typically the antibody is monoclonal. Such a whole antibody is typically an antibody which is produced by any of the methods of producing an antibody which are discussed herein. Typically the antibody is a mammalian antibody, such as a primate, human, rodent (e.g. mouse or rat), rabbit, ovine, porcine, equine or camel antibody. The antibody can be any class or isotype of antibody, for example IgM, but is preferably IgG.

The fragment of whole antibody that can be used in the method comprises an antigen binding site, e.g. Fab or F(ab)$_2$ fragments. The whole antibody or fragment may be associated with other moieties, such as linkers which may be used to join together 2 or more fragments or antibodies. Such linkers may be chemical linkers or can be present in the form of a fusion protein with the fragment or whole antibody. The linkers may thus be used to join together whole antibodies or fragments which have the same or different binding specificities, e.g. that can bind the same or different compounds of formula (I), (II) or (III), or other degradation fragments of bilirubin or biliverdin, or salts thereof. The antibody may be a bispecific antibody which is able to bind to two different antigens (or antigenic surfaces), typically any two of the compounds of formula (I), (II) or (III), or other degradation fragments of bilirubin or biliverdin, or salts thereof, mentioned herein. The antibody may be a 'diabody' formed by joining two variable domains back to back. In one embodiment the antibody is a chimeric antibody comprising sequence from different natural antibodies, for example a humanised antibody.

Generally the method is carried out in an aqueous solution. The sample and/or the antibody may be present is solution in the method. In particular embodiments (some of which are discussed below) the agent or sample is immobilised on a solid support. Typically such a support is the surface of the container in which the method is being carried out, such as the surface of a well of a microtitre plate.

In the method, determining whether the agent binds a compound of formula (I), (II) or (III), or other degradation fragment of bilirubin or biliverdin, or sat thereof, in the sample may be performed any method known in the art for detecting binding between two moieties. The binding may be determined by measurement of a characteristic in either the antibody or the compound of formula (I), (II) or (III), or the other degradation fragment of bilirubin or biliverdin, or salt thereof, that changes when binding occurs, such as a spectroscopic change.

In a preferred embodiment the agent is immobilised on a solid support (such as the supports discussed above). When the sample is contacted with the agent compounds of formula (I), (II) or (III), or other degradation fragments of bilirubin or biliverdin, or salts thereof, bind to the agent. Optionally the surface of the solid support is then washed to remove any compound from the sample which is not bound to agent. The presence of the compound of formula (I), (II) or (III), or the other degradation fragment of bilirubin or biliverdin, or salt thereof, bound to the solid support (through the binding with the agent) can then be determined, indicating that the compound of formula (I), (II) or (III), or the other degradation fragment of bilirubin or biliverdin, or salt thereof, is bound to the agent. This can be done for example by contacting the solid support (which may or may not have the compound of formula (I), (II) or (III), or the other degradation fragment of bilirubin or biliverdin, or salt thereof, bound it) with a substance that binds the compound of formula (I), (II) or (III), or the other degradation fragment of bilirubin or biliverdin, or salt thereof, specifically. This agent may be labelled either directly or indirectly by a detectable label.

Typically the substance is a second agent which is capable of binding the compound of formula (I), (II) or (III), or the other degradation fragment of bilirubin or biliverdin, or salt thereof, in a specific manner whilst the compound of formula (I), (II) or (III), or the other degradation fragment of bilirubin or biliverdin, or salt thereof, is bound to the first immobilised agent that binds the compound of formula (I), (II) or (III), or the other degradation fragment of bilirubin or biliverdin, or salt thereof. This second agent can be labelled indirectly by contacting with a third antibody specific for the Fc region of the second agent, wherein the third agent carries a detectable label.

Another system which can be used to determine the binding between the compound of formula (I), (II) or (III), or the other degradation fragment of bilirubin or biliverdin, or salt thereof, and the agent is a competitive binding system. One embodiment of such a system determines whether the compound of formula (I), (II) or (III), or the other degradation fragment of bilirubin or biliverdin, or salt thereof, in the sample is able to inhibit the binding of the agent to a reference compound which is capable of binding the agent. The reference compound may, for example, be a known amount of labelled compound containing a functional group or groups which the agent recognises. If the compound of formula (I), (II) or (III), or the other degradation fragment of bilirubin or biliverdin, or salt thereof, in the sample is able to inhibit the binding the between the agent and reference compound then this indicates that such a compound of formula (I), (II) or (III), or other degradation fragment of bilirubin or biliverdin, or salt thereof, is recognised by the agent.

Examples of detectable labels include enzymes, such as a peroxidase (e.g. of horseradish), phosphatase, radioactive elements, gold (or other colloid metal) or fluorescent labels. Enzyme labels may be detected using a chemiluminescence or chromogenic based system.

The invention also includes a dipstick which can be used to carry out the method of the invention. The dipstick comprises a porous material capable of chromatographically transporting a liquid and one or more of the agents mentioned herein. When the dipstick is contacted with the sample it draws up liquid from the sample towards a detection region on the dipstick. Proteins in the sample comprising the polymorphisms mentioned herein are detected by their binding to detection region.

In one embodiment the liquid is drawn through a region in the dipstick containing the agents mentioned above. The agents bind to the compound of formula (I), (II) or (III), or the other degradation fragment of bilirubin or biliverdin, or salt thereof, forming an agent/compound complex. This complex is drawn towards the detection region which contains a substance (immobilised on the dipstick) that binds and thus immobilises the complex in the detection region. The substance is typically a specific binding agent (e.g an antibody) that binds either the agent or the compound of the complex. The agent/compound complex is typically detected in the detection region by the use of a label which is attached to the agent.

In another embodiment the compound of formula (I), (II) or (III), or the other degradation fragment of bilirubin or biliverdin, or salt thereof, in the sample is labelled before it is drawn up the dipstick. The labelled compound is then drawn up the dipstick (which has been contacted with sample) and is detected by binding the antibody (which is bound to the detection region).

Typically the label used in the dipstick systems described above is a visually detectable label which becomes visually detectable (i.e. can be seen with the human eye) when enough agent/compound complex becomes immobilised in the detection region. A suitable label is a gold (or other colloidal metal) particle or a fluorophore (e.g. fluoroscein).

In a further aspect the present invention provides a method of purifying blood which comprises irradiating it so as to degrade any photolabile compounds therein. Such purification of blood may be desirable in the treatment of, for example, systemic inflammatory response syndrome (SIRS) or other inflammatory disorders, infections, trauma (particularly muscle trauma where haem from myoglobin may be problematic) or haemolytic conditions.

In one embodiment the photolabile compounds which are degraded are photolabile degradation fragments of bilirubin or biliverdin.

The photolabile compounds may be degraded by contacting the blood with a blood dialyser which incorporates an irradiator.

The present invention is further illustrated, merely by way of example, with reference to the figures in which:

FIG. 1 shows the stimulatory effect of the bilirubin oxidative degradation products (ox-BR) and CSF from SAH patients (CSF-SAH) on the rate of oxygen consumption of the porcine carotid artery (FIG. 1A). The steady state rate of oxygen consumption (after 90 minutes) by the porcine carotid artery (n=3) in the presence of ox-BR (final concentration 1 mg/mL), CSF-SAH (final dilution 1/30) and control (A) is significantly increased in both cases compared to control (*P≦0.05). The time course for the stimulation of oxygen consumption was also similar. Vascular smooth muscle tension development (n=4) is induced by ox-BR (final concentration 1 mg/mL) and CSF-SAH (final dilution 1/30) and can be abrogated by dobutamine (DOB) pre-treatment of carotid artery rings (B). Results are expressed as mean ±SE.

FIG. 2 shows the HPLC elution profile of chloroform extract from crude oxidised BR analysed on Spherisorb reversed phase column.

FIG. 3 shows the possible outline pathways for $H_2O_2$ mediated formation of Box A, Box B and 4-methyl-3-vinylmaleimide from BR or biliverdin. In the pathway leading to Box A production: $R_1$ is —$CH_3$, $R_2$ is —CH=$CH_2$, $R_3$ is —$CH_3$ and $R_4$ is —$CH_2$—$CH_2$—COOH. In the pathway leading to Box B formation: $R_1$ is —CH=$CH_2$, $R_2$ is —$CH_3$, $R_3$ is —$CH_3$ and $R_4$ is —$CH_2$—$CH_2$—COOH. In the pathway leading to 4-methyl-3-vinylmaleimide: R is part of bilirubin molecule.

FIG. 4 shows the haemorrhage in the brain of a rat following BOXes injection.

FIG. 5 shows in vivo vasospasm in a rat brain following BOXes treatment.

FIG. 6 shows rat brain slices following topical application of BOXes.

Figure 1A:
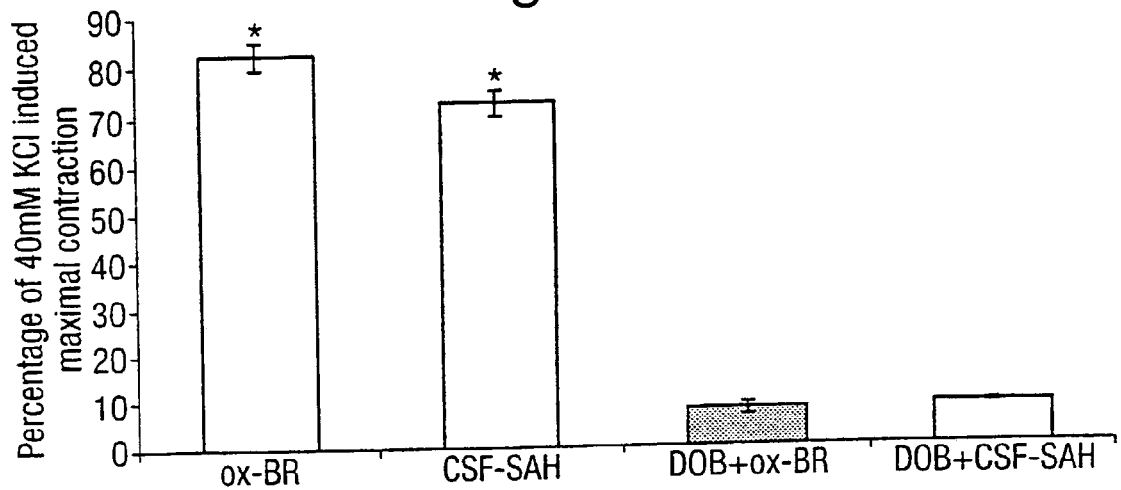

The Examples which follow further illustrate the present invention with reference to the figures.

EXAMPLES

Materials and Methods

Bilirubin Peroxidation Procedure

Bilirubin (mixed isomers, 100 mg, from Sigma Chemical Co.) was suspended with stirring in 25 mL of 5 M NaOH over 4 h at room temperature. The reaction flask was protected from light by aluminium foil. After 4 h the orange suspension of BR had largely dissolved giving a dark green solution. The solution was neutralised using 11 M HCl and 20 mL of 30% $H_2O_2$ was added. The reaction mixture was then incubated in the dark 48 h, at room temperature, resulting in a transparent yellow solution with some precipitation. A portion of this crude mixture was filtered (pore size 0.2 μm), evaporated to dryness and analysed by $^1H$ NMR spectroscopy (500 MHz). Another portion of crude mixture was used for oxygen consumption measurement. For this examination a portion of crude mixture was freeze-dried and re-dissolved in physiological saline solution (PSS, which is described below) to form a final concentration of 1 mg/mL of PSS. The remaining reaction mixture was filtered and extracted 10 times with chloroform [reaction mixture: chloroform (5:1)]. The solution was dried over sodium sulphate and evaporated in vacuo to give a yellow solid. The latter was also analysed by $^1H$ NMR spectroscopy (500 MHz).

HPLC Analyses and Purification

The chloroform extract was dissolved in 50% (v/v) aqueous and purified by HPLC. Experiments were conducted so as to exclude light from samples. Hypersil reversed-phase C18 (250×7 mm) or Spherisorb ODS (2) reversed-phase columns (250×4.6 mm) were equilibrated with 30% (v/v) aqueous acetonitrile at a flow rate pf 2 mL min$^{-1}$ and 1 mL min$^{-1}$, respectively. Elution was performed using 30% to 36% aqueous acetonitrile linear gradient at the same flow rates over 8 min. Fractions were monitored at 320 nm and collected manually. The fractions were freeze dried and stored at −80° C. for further analyses. Each fraction was re-dissolved in 50% (v/v) aqueous acetonitrile, re-injected and re-purified using the same conditions to remove impurities from other fractions. To investigate the light sensitivity of the compounds, purified fractions were exposed to sunlight for 90 min after dissolving 50% (v/v) aqueous and analysed by HLPC.

Spectroscopy

UV/Vis spectroscopy was performed in double distilled $H_2O$ using an Ultrospec 4000 UV/Vis spectrophotometer IR spectra were collected at a 4 cm$^{-1}$ resolution on a Perkin Elmer FT-IR spectrometer A minimum of 256 scans were summed and collected.

Spectra were recorded at temperature of 300 K on a Bruker AMX500 spectrometer (500 MHz) equipped with an inverse-broadband z-gradient probehead. Heteronuclear multiple-bond correlation (HMBC) spectra were recorded with gradient selection and without the use of a low-pass filter so that single-bond correlations could be established simultaneously. These were identified by the characteristic $^1J_{CH}$ doublet structure that is apparent when broadband carbon decoupling is not applied during collection of each of FID. All $^{13}C$ chemical shifts were obtained indirectly from correlation peaks in the 2D experiment Electrospray Ionisation Mass Spectrometry and Exact Mass Measurements.

Electrospray ionisation mass spectra were measured on a Micromass BioQ II-ZS triple quadrupole mass spectrometer equipped with an electrospray interface. Samples (10 μL) were introduced into the electrospray source via a loop injector. Positive ion spectra were run from a solution in water/acetonitrile (1:1 v/v) containing 0.2% (v/v) formic acid at a cone voltage of +30V. Negative ion mass spectra were run from a solution water/acetonitrile (1:1 v/v) at cone voltages of −10V and −15V, the source temperature was set at 40° C. High-resolution exact mass spectra were recorded on a Micromass Autospec 5000 OA-Tof mass spectrometer in the chemical ionisation mode with ammonia as the reagent gas.

Cerebrospinal Fluid (CSF) Collection

CSF was collected from SAH patients either at the time of surgery or through the lumbar drain inserted to relieve intracranial pressure.

Tissue Collection and Measurements of Oxygen Consumption

Porcine carotid artery were collected from an abattoir within 30 minutes of death, rinsed and immersed in PSS at 4° C., and immediately transported to the laboratory. Arteries were then trimmed of excess connective tissue and adventitia to be stored in PSS at 4° C. until use. The PSS was changed every 12 hours and the vessels were kept for up to 4 days. The PSS contained the following: 118 mmol/L sodium chloride, 25 mmol/L sodium hydrogen carbonate, 5.76 mmol/L potassium chloride, 2.5 mmol/L calcium chloride, 1.2 mmol/L magnesium sulphate, 0.5 mmol/L monobasic sodium phosphate, and 11.1 mmol/L glucose. The solution was oxygenated by bubbling with 95% oxygen and 5% carbon dioxide to maintain a pH of 7.4.

The rate of the oxygen consumption was determined using a Hansatech Instruments (Norfolk, United Kingdom) Clark oxygen electrode. Carotid artery rings approximately 0.2 cm long were vigorously rubbed to remove the endothelial cells and were added to the water-jacketed chambers containing PSS at 37° C. The rates of oxygen consumption were measured before and after the addition of crude mixture of the BR oxidative degradation products (final concentration 1 mg/mL of PSS). $CSF_{SAH}$ (final dilution 1/30) or 4-methyl-3-vinylmaleimide (purified on HPLC, freeze-dried and then re-dissolved in PSS). The results are presented as µmol $O_2$ consumed per minute per gram dry weight, assuming that the solubility of oxygen in PSS at 37° C. is 0.202 µmol/mL or as percentage increase in oxygen consumption in comparison with oxygen consumption by carotid artery alone.

Force Measurements

Isometric force measurement were performed on porcine carotid artery rings to assess functional parameters during exposure to various compounds. The methods used were those used by J F Clark et al., J. Vasc. Res., 1995, 32, 24–30. KCl induced contraction is used as maximal isometric tension generation and results are reported as percentage of KCl maxima obtained for each carotid.

Statistical Analysis

The programme ANOVA was used to statistically evaluate the data, and values were considered to be significantly different if $p<0.05$.

Results

Oxygen Consumption Measurements

Figure 1B:
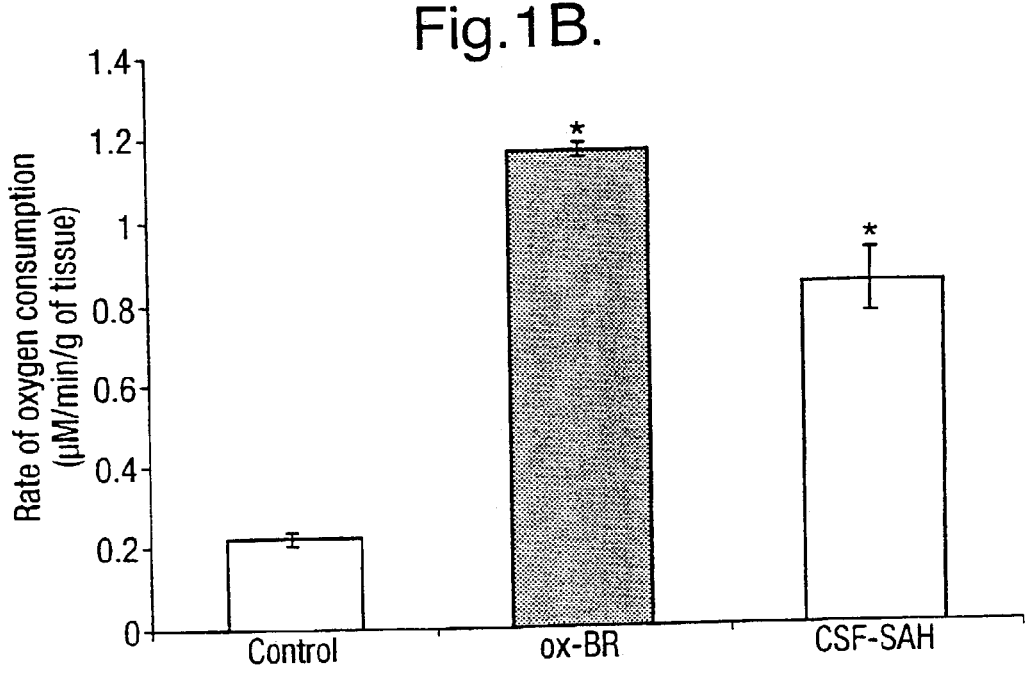

Crude oxidised BR at concentration of 1 mg/mL PSS increased oxygen consumption of the porcine carotid artery by about 3.6 fold in 90 min (FIG. 1). $CSF_{SAH}$ stimulated an increase in the rate of oxygen consumption in a similar manner as crude oxidised BR (FIG. 1). High doses of either crude oxidised BR or $CSF_{SAH}$ from patients with SAH inhibited oxygen consumption by carotid artery or even inhibited the tissue's oxygen consumption. CFS from healthy controls or control solutions for crude oxidised BR did not exhibit any activity. Chloroform extracts of crude oxidised BR and 4-methyl-3-vinylmaleimide also stimulated oxygen consumption. However, it was not possible determine the concentration of 4-methyl-3-vinylmaleimide used in the experiments because of the small amount of material obtained.

HPLC Analyses and Purification.

Following the observation that biological activity was extractable into chloroform the extracts were analysed and purified by HPLC. FIG. 2 shows the separation pattern for three isolated compounds: Box (Bilirubin oxidised) A, Box B and 4-methyl-3-vinylmaleimide (Box C). Reaction of biliverdin with $H_2O_2$ also resulted in production of the same compounds, as judged by their retention times.

Box A, Box B and 4-methyl-3-vinylmaleimide were light sensitive. When exposed to sunlight for 90 min, as judged by HPLC, the intensity of their peaks significantly decreased. $^1H$ NMR analyses of Box A and Box B after sunlight exposure for 90 min also indicated degradation to a number of products. In contrast, Box A, Box B and 4-methyl-3-vinylmaleimide were relatively heat-stable when kept 60° C. for 2 h as judged by HPLC analyses.

Spectroscopic Analyses

Figure 3:
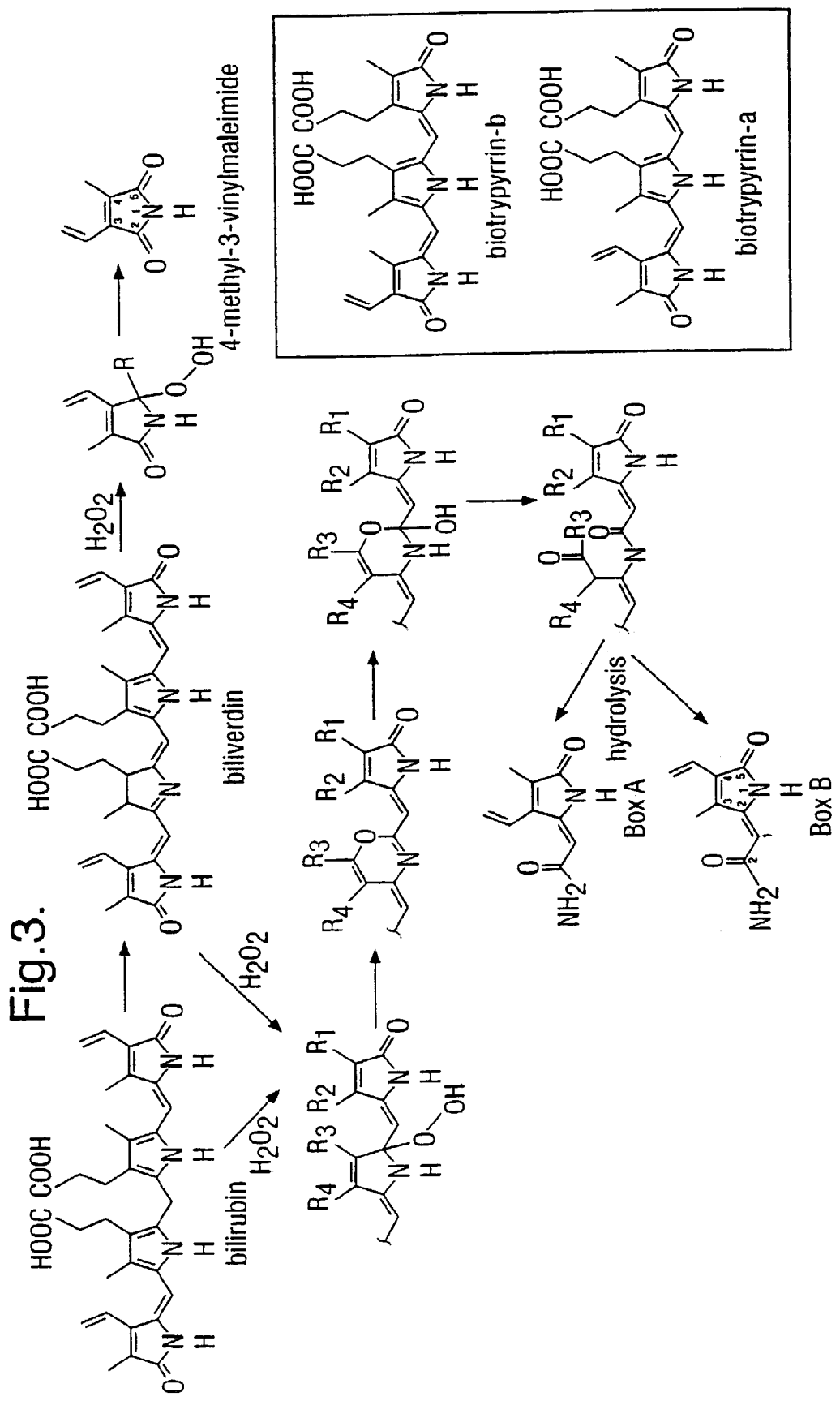

Box A: 4-methyl-5-oxo-3-vinyl-(1,5-dihydroppyrrol-2-ylidene)acetamide (FIG. 3). UV/Vis spectroscopy: $\lambda_{max}$ 215 nm and 300 nm. IR spectroscopy: 3434.0(N—H), 1698.2 (C=O, lactam), 1666.4 (C=O; amide), 1430.5 and 1292.7 $cm^{-1}$. $^1H$ and $^{13}C$ NMR assignments (500 MHz) were established from a long-range heteronuclear $^1H$-$^{13}C$ 2D correlation (HMBC) experiment (Table 1).

TABLE 1

| | $^1H$ NMR (100% $CD_3CN$)[a] | $^{13}C$ NMR ($CD_3CN/D_2O$)[b] |
|---|---|---|
| 1 | 9.69 | — |
| 2 | — | 147.0 |
| 3 | — | 140.7 |
| 4 | — | 131.5 |
| 5 | — | 173.8 |
| 1' | 5.62 | 99.1 |
| 2' | — | 169.7 |
| 3-vinyl-CH | 6.57 | 125.3 |
| 3-vinyl-$CH_2$ | 5.68 5.71 | 124.6 |
| 4-Me | 1.98 | 9.1 |
| $NH_2$ | 6.37/5.86 | — |

[a]Referenced to residual $CH_3CN$ at 1.94 ppm
[b]Externally referenced to TSP at 0.0 ppm The proton spectrum (in $CD_3CN$) demonstrated the presence of a single vinylic CH=$CH_2$ group plus a sharp singlet consistent with a remote alkene moiety. Also present in this region were two, broad resonances each corresponding to a single proton, which were not present in later $D_2O$/acetonitrile spectra. These were suggestive of a primary amide $NH_2$ group in which the two protons were differentiated as a result of restricted amide bond rotation. A further broad, exchangeable resonance, also corresponding to a single proton, was observed at 9.69 ppm indicating the presence of a core pyrrole ring structure. These data, together with the presence of an additional three-proton singlet at 1.98 ppm, suggested a pyrrole derived core was intact in this fragment and that it carried a methyl and vinylic group, and hence that it resulted from oxidative cleavage site was consistent with molecular mass, and was confirmed from connectivities observed in long-range heteronuclear $^1H$-$^{13}C$ 2D correlation (HMBC) experiments (in 3:7 $CD_3CN$:$D_2O$, due to limited solubility). All observed correlations were consistent with Box A. Notably, the methyl singlet correlated strongly to a carbonyl at 173.8 ppm whilst the remote alkene proton correlated to the amide carbonyl at 169.7 ppm. These data also established the location of the methyl group adjacent to the carbonyl of the ring. The assignment of the exocyclic double bond was not possible. Mass spectrometry: m/z 179.20 ($MN^+$; electroionization); m/z 179.082163 ($MH^+$), calc. mass 179.082053 (high-resolution mass spectrometry). Molecular formula: $C_9H_{11}N_2O_2$.

Figure 4A:
FIG. 4a shows a non-BOXes (control) group rat brain and FIG. 4b shows a BOXes group rat brain.

Box B: 3-methyl-5-oxo-4-vinyl-(1,5-dihydropyrrol-2-ylidene)acetamide (FIG. 4). UV/Vis spectroscopy: $\lambda_{max}$ 215 nm and 310 nm. IR spectroscopy 3435.7 (N—H), 1654.1 (C=O; lactam) and 1647.9 (C=O; amide) $cm^{-1}$. $^1H$ and $^{13}C$ NMR assignments (500 MHz) were established from a long-range heteronuclear $^1H$-$^{13}C$ 2 D correlation (HMBC) experiment (Table 2).

TABLE 2

| | $^1H$ NMR (100% $CD_3CN$)[a] | $^{13}C$ NMR ($CD_3CN/D_2O$)[b] |
|---|---|---|
| 1 | 9.49 | — |
| 2 | — | 147.9 |
| 3 | — | 142.7 |

TABLE 2-continued

| | $^1$H NMR (100% $CD_3CN$)[a] | $^{13}$C NMR ($CD_3CN/D_2O$)[b] |
|---|---|---|
| 4 | — | 129.2 |
| 5 | — | 173.0 |
| 1' | 5.55 | 99.0 |
| 2' | — | 170.2 |
| 4-vinyl-CH | 6.62 | 125.7 |
| 4-vinyl-$CH_2$ | 5.52, 6.32 | 122.4 |
| 3-Me | 2.07 | 9.1 |
| $NH_2$ | 6.37/5.86 | — |

[a]Referenced to residual $CH_3CN$ at 1.94 ppm
[b]Externally referenced to TSP at 0.0 ppm The proton spectra demonstrated the same principle features as for Box A, with the most significant being in the shift dispersion of the vinylic protons, HMBC data (in 3:7 $CD_3CN:D_2O$) confirmed the presence of the same core structure but indicated the relative position of the methyl and vinyl groups were switched. The CH proton of the vinyl group now correlated strongly to the carbonyl of the pyrrole ring at 173.0 ppm. This isomeric fragment would therefore derive from oxidative cleavage from the other end of the BR molecule to that which produced Box A. The assignment of the exocyclic double bond stereochemistry was not possible. Mass spectrometry: m/z 179 ($MH^-$, electroionization); m/z 179.082021 ($MH^-$), calc. mass 179.082053 (high-resolution mass spectrometry). Molecular formula: $C_9H_{11}N_2O_2$.

The shift patterns observed for the methyl and vinyl protons in Box A and Box B bear a striking similarity with those of the tri-pyrrole fragments: biotripyrrin-a and biotripyrrin-b (FIG. 3) isolated by Yamaguchi et al (Yamaguchi 94). In both cases, the vinylic protons in particular display characteristic behaviour, with the geminal pair appearing essentially coincident when they sit on the opposite side of the pyrrole core to the pyrrole carbonyl, but displaying significant dispersion when adjacent to this carbonyl group. These similarities further support the assigned relative location of-methyl and vinyl groups in Box A and Box B.

4-Methyl-3-vinylmaleimide: IR spectroscopy: 3436.2 (N—H), 2103.9, 1773.7, 1713.0, 1639.6 $cm^{-1}$. $^1$H and $^{13}$C NMR assignments (500 MHz) were established from a long-range heteronuclear $^1$H-$^{13}$C 2D correlation (HMBC) experiment (Table 3).

TABLE 3

| | $^1$H NMR[a] | $^{13}$C NMR[b] |
|---|---|---|
| 1 | 7.19 | — |
| 2 | — | 170.2 |
| 3 | — | 134.3 |
| 4 | — | 136.7 |
| 5 | — | 171.4 |
| 3-vinyl-CH | 6.55 | 124.2 |
| 3-vinyl-$CH_2$ | 6.40, 5.73 | 125.9 |
| 4-Me | 2.07 | 8.3 |

Referenced to $CDCl_3$ at 7.27[a] and 77.0[b] ppm

4-Methyl-3-vinylmaleimide was soluble in chloroform and afforded a simple $^1$H spectrum, demonstrating the presence of a vinyl group (in which the geminal pair were well dispersed), a methyl group and a broad resonance at 7.19 ppm. HMBC spectra demonstrated correlations from the vinyl CH proton and from the methyl group to different carbonyl centres, and readily identified the fragment as having the structure of 4-methyl-3-vinylmaleimide. The dispersion of the vinylic protons is again consistent with these being adjacent to a carbonyl group within the pyrrole core. Negative ion mass spectrometry m/z 135.9. $^1$H NMR (500 MHz) and mass spectrometry data were consistent with those reported for 4-methyl-3-vinylmaleimide.

BR was shown to react with hydrogen peroxide, using a procedure designed to mimic severe oxidative stress, to give various fragmentation products. The crude oxidised BR solution stimulated oxygen consumption of vascular smooth muscle from the porcine carotid artery in the absence of endothelial layer. $CSF_{SAH}$ also stimulated oxygen consumption in vascular smooth muscle. Comparison of $CSF_{SAH}$ with the BR oxidative degradation products in the oxygen consumption assays revealed that they behaved in a similar manner (FIG. 1). $CSF_{SAH}$ and the BR oxidative degradation products induced stimulation of oxygen consumption following addition to the chamber with the artery. In addition, high doses of both $CSF_{SAH}$ and the BR oxidative degradation products inhibited the rate of oxygen consumption or even killed vascular smooth muscle. Isometric force measurement experiments confirmed that the change in metabolism mirrored the changes caused by $CSF_{SAH}$ and the BR oxidation products.

The bioactive compounds from both $CSF_{SAH}$ and oxidised BR were both extractable into chloroform. Three photolabile compounds were isolated by HPLC: 4-methyl-5-oxo-3-vinyl-(1,5-dihydropyrrol-2-ylidene)acetamide (Box A) and 4-methyl-3-vinylmaleimide and 3-methyl-5-oxo-4-vinyl-(1,5-dihydropyrrol-2-ylidene)acetamide (Box B). Along with Box A and Box B the monopyrrole derivative 4-methyl-3-vinylmaleimide was also isolated. 4-Methyl-3-vinylmaleimide is known to be formed during photooxidation of biliverdin, as well as in the reaction of $H_2O_2$ with ferriprotoporphyrin IX or by chromic acid with BR. The reaction mixture was protected from light, therefore it is assumed that 4-methyl-3-vinylmaleimide is formed in the reaction of $H_2O_2$ with BR or biliverdin. Nevertheless, traces of 4-methyl-3-vinylmaleimide may be produced by incidental light exposure. Although 4-methyl-3-vinylmaleimide has not been detected directly in vivo, its hydrolysis has been found in jaundiced neonates undergoing phototherapy.

Box A and Box B cannot be formed using the mechanism leading to biotripyrrins a and b, since formation of official Box A and Box B requires nitrogen from pyrrole rings. Studies on singlet oxygen mediated photolytic degradation of BR have indicated a mechanism involving electron transfer of excited state BR with ground state dioxygen. A number of products including biliverdin, 4-methyl-3-vinylmaleimide and simple aliphatic acids have been identified. Whether or not biliverdin is an intermediate in some or all of the fragmentation products is unclear, but they, like BR are not light stable.

A possible mechanism of Box A, Box B and 4-methyl-3-vinylmaleimide during photooxidation is proposed in FIG. 3. A BR-dioxetane has been proposed as an intermediate to 4-methyl-3-vinylmaleimide during photooxidation. However, the intermediates of such species seems less likely in $H_2O_2$ mediated oxidation. Attack of $H_2O_2$ at C-4 or C-16 to give the peroxide shown in FIG. 3, followed by Crigee rearrangement and hydrolysis to give 4-methyl-3-vinylmaleimide may be more likely. The mechanism of initial attack of peroxide is uncertain, with formation of a (radical) cation derivative of BR or biliverdin as a possibility. Similarity, formation of peroxides at C-6 or C-14 followed by rearrangement and hydrolysis can lead to Box A and Box B.

Like 4-methyl-3-vinylmaleimide, which has been shown to react with thiols, including glutathione, Box A and Box B are alkylating agents (Michael acceptors). It is possible they exert biological activity leading to vasospasm via an alkylation process, e.g. affecting cellular phosphatase/kinase systems.

BR oxidative degradation products exhibits biological activity and may play a role in pathogenesis of arterial vasospasm following haemorrhage. Oxidation of BR leads to production of BR-derived fragments which present in $CSF_{SAH}$ from SAH patients.

Evidence for the Presence of Box A in Human Cerebral Spinal Fluid (CSF) Method

Double deionised water (100 ml) was added to 45 ml dry volume of freeze dried CSF and stirred in the dark for 45 mins. Whilst stirring continuously in the dark, urea (20 g) was then added to the (partially) reconstituted CSF to give an approximate concentration of 3M urea. After addition of urea, the solution was stirred for a further 5 mins to give a fully reconstituted solution of CSF with no solid extract. 500 ml of chloroform was then added to this solution whilst stirring in the dark. The solution was then stirred for one hour then centrifuged at 2800 rpm for 5 mins. The chloroform layer was then collected and dried over anhydrous magnesium sulphate in the dark. The magnesium sulphate was removed by filtration in the dark and the chloroform removed by rotary evaporation in vacuo in the dark. The resultant solid extract was redissolved in 250 µl of 1:1 acetonitrile:deionised water. The resultant solution was then configured at 13000 rpm for 15 mins.

The supernatant was then analysed by HPLC equipped with a photodiode array detector. The experimental conditions were as follows: 100 µl of the 1:1 acetonitrile:deionised water solution was analysed by HPLC using a Phenomenex Phenosphere 5 micron ODS2 80A 250 mm×4.6 mm column. The following gradient was run with a flow rate of 1 ml a minute.

| Time in minutes | % Buffer A<br>10 mM Ammonium bicarbonate in 50% Acetonitrile/50% deionised water | % Buffer B<br>10 mM Ammonium bicarbonate in deionised water |
| --- | --- | --- |
| 0–5 | 50 | 50 |
| 5–30 | 50–100<br>(linear gradient) | 50–0<br>(linear gradient) |
| 30–35 | 100 | 0 |
| 35–45 | 50 | 50 |

At a retention time of ca. 5 min 20 secs a compound with UV profile with absorbance maxima at 212 and 297 nm was observed. The profile was the same as that of a reference sample Box A (prepared synthetically). The presence of Box A in CSF was further confirmed by analysis of CSF samples doped with reference Box A.

Mortality Study Using Bilirubin Oxidation Products (BOXes)

A mortality study was performed in which lysed autologus blood was injected into the cisterna magna of anesthetized rats. In one group of rats the lysed autologous blood was supplemented with a standardized amount of BOXes and in the other group BOXes were absent (with constant volumes of solutions (50 µL) injected in both groups). The BOXes group contained 7 rats and the non-BOXes (control) group contained 12 rats. The BOXes were prepared as previously described and the same dose administered as used in the oxygen consumption measurements described above.

In the BOXes group, 5 of the 7 rats died within 24 hours whereas in the non-BOXes group none of the 12 rats died. This is a significant increase in mortality ($P \leq 0.001$) as determined with the Fishers Exact Test.

Figure 4B:

The cause of death was believed to be intense vasoconstriction causing ischemic damage as well as visible signs of haemorrhage. The haemorrhage is likely to be due to venous hypertension and subarachnoid haemorrhage (see FIG. 4b showing the haemorrhage in the brain of a rat following BOXes injection).

Vasospasm in Rats Caused by BOXes

Figure 5A:
FIG. 5a shows the rat brain with the dura intact and FIG. 5b shows that after BOXes have been dropped onto the surface of the dura there is obvious vasospasm (arrow).
Figure 5B:
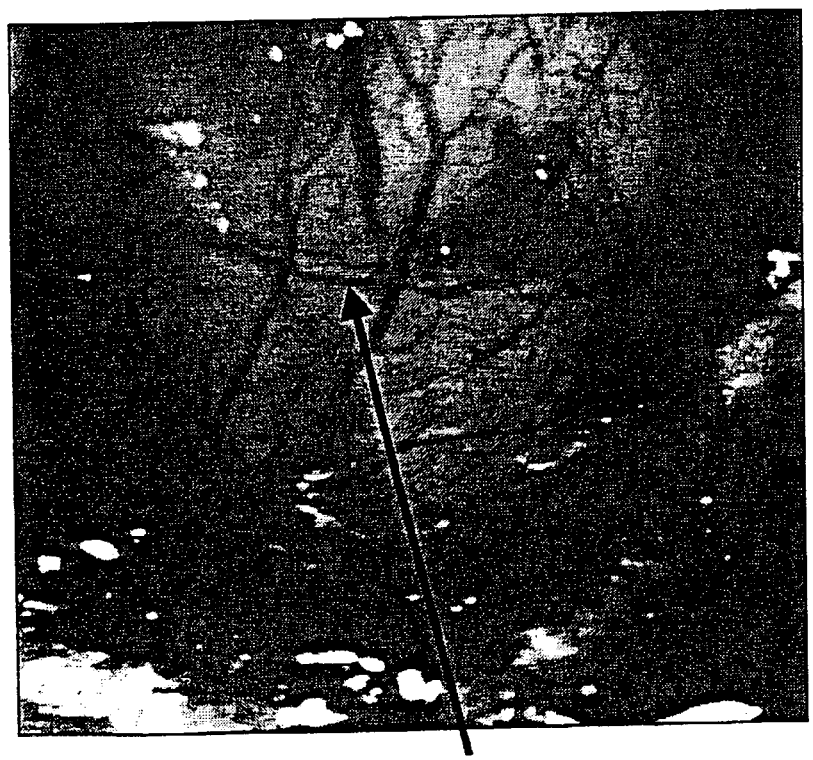

A lower dose of BOXes than that injected into the cisterna magna in the mortality study was dropped onto the surface of a rat brain. Typically, 200 µL of BOXes was dropped on to the surface of the brain but a significant proportion of the solution simply washed over the surface of the brain's dura matter. A vasospasm response was observed in less than 10 minutes (see FIG. 5b).

Induction of Heat Shock Proteins by BOXes

Figure 6A:
FIG. 6a shows a control rat brain slice and FIG. 6b shows HSP25 expression in a rat brain slice after treatment with BOXes.
Figure 6B:
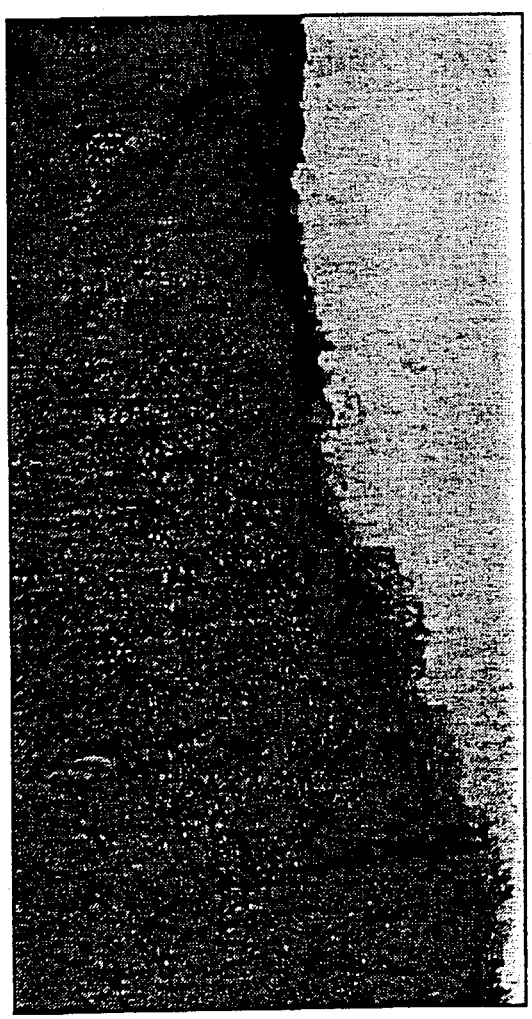

The brains from the animals used in the vasospasm study were probed for heat shock proteins (HSP); HSP 32, HSP 70 and HSP 25. All of these heat shock proteins were found to be induced in the underlying cortex where the BOXes were applied and where the vasospasm was observed. HSP 25 expression localized to the blood vessels in these regions was also observed (see FIG. 6b).

The induction of HSPs was not evident in the control animals (bilirubin or saline). The induction of HSPs was localized to the area where the BOXes were applied.

What is claimed is:

1. A method for diagnosing vasospasm or vasoconstriction in a host comprising determining the presence or absence of a compound of formula (I)

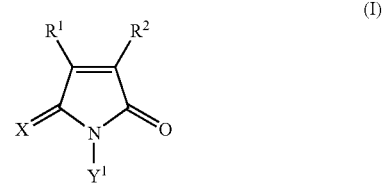

wherein when X is =CH(C=O) NH₂, Y¹ is hydrogen, and one of R¹ and R² is methyl and the other is —CH=CH₂, or When X is =O, Y¹ is hydrogen, R¹ is —CH=CH₂ and R² is methyl;

formula (II)

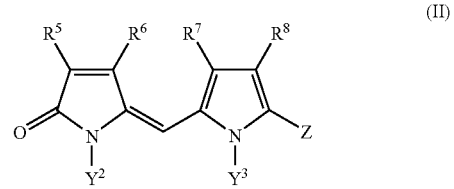

wherein each of $Y^2$ and $Y^3$ is hydrogen, Z is —$CH_2$(C=O)CH(($CH_2$)$_2CO_2H$)(C=O)$CH_3$ one of $R^5$ and $R_6$ is methyl and the other is —CH=$CH_2$, $R^7$ is methyl, $R^8$ is ($CH_2$)$_2CO_2H$;

formula (III)

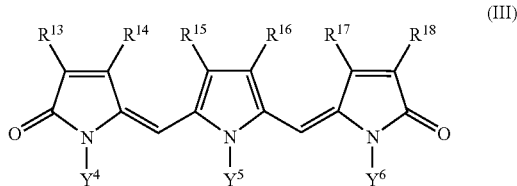

wherein one of $R^{13}$ and $R^{14}$ is methyl and the other is —CH=$CH_2$, each of $R^{15}$ and $R^{18}$ is methyl and each of $R^{16}$ and $R^{17}$ is —($CH_2$)$_2CO_2H$;

or other degradation fragment of bilirubin or biliverdin, or salt thereof, wherein the presence of the compound of formula (I), (II) or (III), or the degradation fragment of bilirubin or biliverdin, indicates that the host has vasospasm or vasoconstriction.

2. A method according to claim 1, which method comprises (c) contacting a sample from the host with an agent that binds to the compound of formula (I), (II) or (III), or the other degradation fragment of bilirubin or biliverdin, or salt thereof, and (d) detecting whether the agent binds to components in the sample, thereby determining the presence or absence of the compound of formula (I), (II) or (III), or the other degradation fragment of bilirubin or biliverdin, or salt thereof.

3. A method according to claim 2 wherein the agent is an antibody which is specific for the compound of formula (I), (II) or (III), or the other degradation fragment of bilirubin or biliverdin, or salt thereof.

4. A method according to claim 3 wherein the antibody is labeled.

* * * * *